United States Patent

Nagy

[11] Patent Number: 5,835,974
[45] Date of Patent: Nov. 10, 1998

[54] METHOD AND MEANS FOR BLENDED MULTI-COMPONENT GAS CALIBRATION AND DIAGNOSIS OF MULTIPLE GAS ANALYZERS

[75] Inventor: Donald B. Nagy, Canton, Mich.

[73] Assignee: General Motors Corporation, Detroit, Mich.

[21] Appl. No.: 293,630

[22] Filed: Aug. 22, 1994

[51] Int. Cl.$^6$ .................................................. G01N 30/02
[52] U.S. Cl. ............................................................ 73/1.06
[58] Field of Search ........................... 73/1 G, 1 R, 1.06; 137/602, 605, 606, 597

[56] References Cited

U.S. PATENT DOCUMENTS

| 3,359,784 | 12/1967 | Jorre et al. | 73/1 G |
| 3,854,876 | 12/1974 | Rankine et al. | |
| 4,498,496 | 2/1985 | Barcellona et al. | 73/1 G |
| 4,977,776 | 12/1990 | Shindo et al. | 73/1 G |
| 5,239,856 | 8/1993 | Mettes et al. | 73/1 G |
| 5,285,672 | 2/1994 | Yao | 73/1 G |
| 5,333,487 | 8/1994 | Kimura et al. | 73/23.31 |

OTHER PUBLICATIONS

SAE Paper, 930141 "A Sampling System for the Measurement of PreCatalyst Emissions from Vehicles Operating Under Transient Conditions" McLeod et al Mar. 1–5, 1993.

*Primary Examiner*—Robert Raevis
*Attorney, Agent, or Firm*—Charles K. Veenstra

[57] ABSTRACT

A gas flow system for an emission analysis bench includes a source of blended calibration span gas using a single span tree connected with all the analyzers so that a method of simultaneous calibration or diagnosis of all the analyzers may be carried out and the need for multiple span trees connected with various separate span gases is avoided. The method includes concurrent delivery of one or more divisions of the span gases to all the analyzers to obtain intermediate data points from the analyzers. A further step of using a precalibrated or linear analyzer, such as the flame ionization detector (FID hydrocarbons analyzer) of the system, to accurately determine the percentage ratio of intermediate divide points obtained by mixing various amounts of zero gas with the span gas simplifies the calibration procedure and eliminates the need for an expensive gas divider.

10 Claims, 5 Drawing Sheets

METHOD AND MEANS FOR BLENDED MULTI-COMPONENT GAS CALIBRATION AND DIAGNOSIS OF MULTIPLE GAS ANALYZERS

TECHNICAL FIELD

This invention relates to engine exhaust emission testing, and more particularly to calibration and diagnosis of exhaust gas analyzers on a bench or at a common site. In particular the invention relates to a method and means for concurrent calibration or diagnosis of multiple analyzers for diverse gases.

BACKGROUND

It is known in the art relating to engine exhaust emission testing to provide one or more test benches at a test site. Each bench includes a plurality of exhaust gas analyzers, each adapted to determine the concentration of a particular form of residual gas in a diluted sample of engine exhaust.

To assure accuracy of the data obtained, it is necessary to periodically calibrate each of the gas analyzers on the benches at a test site. In current practice, this is done by connecting each analyzer with a source of a non-reactive zero gas and a separate span gas for each analyzer range to be calibrated having a known concentration of the gas to which each analyzer is responsive. These are supplied to each respective analyzer through a series of valves called a span tree. To span or zero the analyzer, the proper valves are sequentially energized to route the zeroing or calibrating gas samples to the analyzer. Divisions of the span gas mixed with various percentages zero gas are then supplied to obtain intermediate analyzer readings.

The present method for obtaining the intermediate points and calibrating the analyzers on an emission analysis bench having, for example, NOx, HC, CO and CO2 analyzers, is as follows:

1) Beginning with the TNOX analyzer, the proper span gas is routed through the span tree to a capillary gas divider located in an analyzer bench. The gas divider then divides down (dilutes) the concentration for the first divide point, for example, 15 percent of the span gas value. The divided gas is then routed to the gas analyzer.
2) The reading from the NOX analyzer is recorded.
3) The foregoing procedure is repeated for nine additional divide points (concentrations).
4) Steps 1–3 are then repeated for each of the remaining (HC, CO and CO2) analyzers in the bench.
5) Using the data gathered, the least squares best fit equation is determined for each analyzer and is programmed into the computer for correction of the analyzer readings.

This procedure is required to calibrate the analyzers on only one bench. A similar procedure using only one or two intermediate points is employed to check or diagnose the accuracy of the analyzers between calibration periods. These calibration and diagnosis procedures are time consuming and expensive. They also require extensive plumbing and control equipment for connecting each bench to multiple span gas sources and a separate span tree for varying the concentrations of the particular span gas supplied to each of the analyzers. Since a test site may contain as many as seven analysis benches, the time, expense and capital investment required for calibrating all the analyzers is significant. The requirements for and examples of bag type exhaust emission analysis systems, including their operation and calibration, are covered in detail in the Code of Federal Regulations, 40 CFR parts 86–99. Other types, such as instantaneous engine out, intermediate and tailpipe emission testing systems are similarly designed.

SUMMARY OF THE INVENTION

The present invention provides a simplified apparatus and method for simultaneously calibrating or diagnosing all the analyzers on one bench or location which substantially reduces the time for and the hardware, physical size and cost of the procedure and the required equipment. Instead of using a separate and distinct span gas for each analyzer range, this method provides a blended gas. In the case of the exemplary four analyzer bench, a quad-blend gas containing HC, CO, CO2 and NOx is supplied to all the analyzers in a range of concentrations as before. However, only one span tree is needed and the calibration process is significantly shortened. Also the gas supply is simplified by use of a single blended gas and the bench plumbing and equipment are reduced.

These and other features and advantages of the invention will be more fully understood from the following description of certain specific embodiments of the invention taken together with the accompanying drawings.

BRIEF DRAWING DESCRIPTION

In the drawings:

FIG. 1 is a schematic diagram showing a conceptual layout of an emission analysis bench system having a quad-blend span gas calibration supply according to the invention;

FIGS. 2A and 2B comprise a schematic diagram showing in detail emission analysis bench mounted equipment for the system of FIG. 1; and FIGS. 3A and 3B comprise a schematic diagram similar to FIGS. 2A and 2B but showing the bench mounted equipment required for the prior art system using multiple span gas sources.

DETAILED DESCRIPTION

Figure 1:
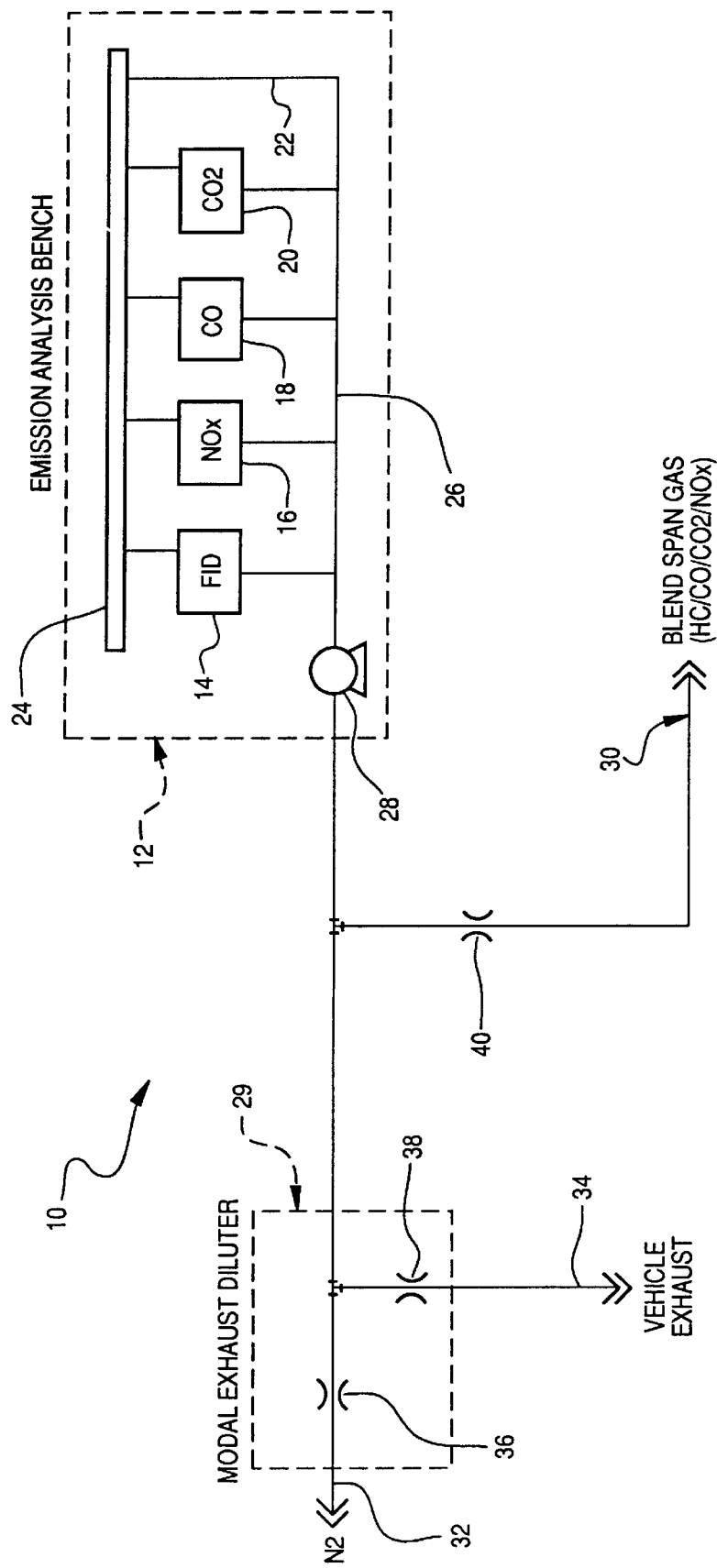

Referring now to the drawings in detail, numeral 10 generally indicates the gas flow system of an emission analysis bench 12 used for testing the tailpipe exhaust emissions of automotive vehicles. It should be understood, however, that the invention could as well be applied to other types of emission analysis benches such as bag, engine out and intermediate types in addition to tailpipe emission analysis benches.

As seen in FIG. 1, the bench 12 mounts four distinct emission analyzers, an FID (flame ionization detector) analyzer 14, an NOx analyzer 16, a CO analyzer 18 and a CO2 analyzer 20. The FID analyzer 14 serves in operation to measure the concentration of hydrocarbons (HC) in samples of vehicle exhaust supplied to the system 10. Similarly, the NOx analyzer measures the concentration of nitrogen oxides, the CO analyzer measures the concentration of carbon monoxide and the CO2 analyzer measures the concentration of carbon dioxide in the vehicle exhaust samples.

The analyzers and a bypass line 22 are connected between an exhaust manifold 24 and a supply manifold 26. A sample pump 28 is connected between the supply header 26 and a modal exhaust mini-diluter 29 as well as a blended span gas supply 30 according to the invention. The diluter 29 connects with both a source 32 of nitrogen (N2) and a source 34 of vehicle exhaust gas from which exhaust samples may be obtained for testing. Mass flow controllers 36, 38, 40 are located in the lines from each of the nitrogen, exhaust and span gas sources, 32, 34, 30 respectively.

The analyzers, pump and mass flow controllers may be of any suitable commercially available types. The mini-diluter 29 may be, for example, similar to that described in SAE technical paper 930141 published Mar. 1, 1993. The blended span gas supply may include one or more blends of diluted HC, CO, CO2 and NOx gases. Each of these diluted gases is an accurately prepared mixture of a non-reactive zero gas with a known ratio of the reactive gas to be tested for, such as HC, CO, etc. The diluted gases are then blended into a single span gas having span concentrations of all the desired reactive gases in a single supply. If desired, more than one blended span gas may be provided for optional use having differing reactive gases in the blend and/or differing span concentrations for calibrating the analyzers over different ranges.

In operation of the system shown in FIG. 1, exhaust gas samples from a vehicle exhaust system (tailpipe) are diluted by nitrogen gas (N2) in the mini-diluter 29 to provide diluted samples adequate for instantaneous testing in the analysis bench 12. The samples are forced by the pump 28 into the header 26 and delivered continuously to the four analyzers 14, 16, 18, 20 for instantaneous computerized analysis of the concentrations of HC, NOx, CO, and CO2 gases.

To calibrate the analyzers for the system, exhaust sample line 34 is closed and a calibration span gas is supplied from one of the blended span gases formed according to the invention and available from the blended span gas supply 30. The blend preferably includes all the gases to be tested for in concentrations equal to the maximum test range to be used in each of the respective analyzers. The analyzers are calibrated simultaneously, first by zeroing the analyzers by concurrently supplying all the analyzers with non-reactive N2 gas. The span of the high points of the analyzers respective ranges are determined by concurrently supplying the blended span gas full strength to all the analyzers and recording their readings.

A suitable number of intermediate points, such as each ten percent from 10–90 percent, are then determined by dividing (diluting) the span gas by mixing with it nonreactive N2 gas sufficient to obtain each of the desired percentages of the full strength span gas, simultaneously supplying each of the divided calibration gas samples concurrently to all the analyzers and recording the readings. The recorded data are then used to determine a least squares best fit equation for each of the span gas percentages and the computer is programmed to correct the analyzer readings accordingly.

A calibrating system according to the invention has several advantages over the prior arrangements known in the art. The amount of equipment required for the system is greatly reduced as will be made clear from the subsequent discussion of FIGS. 2A–B and 3A–B. This is partly due to the use of the blended span gas or gases formed according to the invention.

A further advantage is that expensive additional gas dividers needed for the prior systems are not required with the method of simultaneous calibration of this invention. Instead, the calibration blended gas is divided using the mass flow controllers 36, 40 to obtain approximate intermediate percentage points. The actual percentages for each sample are then determined by the readings of the flame ionization detector (FID) analyzer which gives a linear output. Alternatively, another previously calibrated analyzer or one having an accurate linear output could be used for determining the actual percentages. These actual percentages are then used in determining the readings of the other analyzers which were checked using the same gas samples.

Another clear advantage is that the time required for calibrating the analyzers is greatly reduced by the simultaneous method of calibration instead of the sequential method using separate span gas for each analyzer as previously required.

It should be apparent that a simplified version of the method used for calibration may be used for diagnosis of the operation of any or all of the analyzers when desired between calibration periods. Checking of one or two points on the analyzer readout using the described steps will likely be adequate to assure that the analyzers are continuing to operate along the calibration curve previously determined or to diagnose any deviation which may require correction.

FIGS. 2A–B and 3A–B disclose in detail the schematic layout and components used for one bench of a blended calibration gas system according to the invention and a prior art system respectively. The great difference in the amount of equipment required is immediately apparent.

Figure 2A:
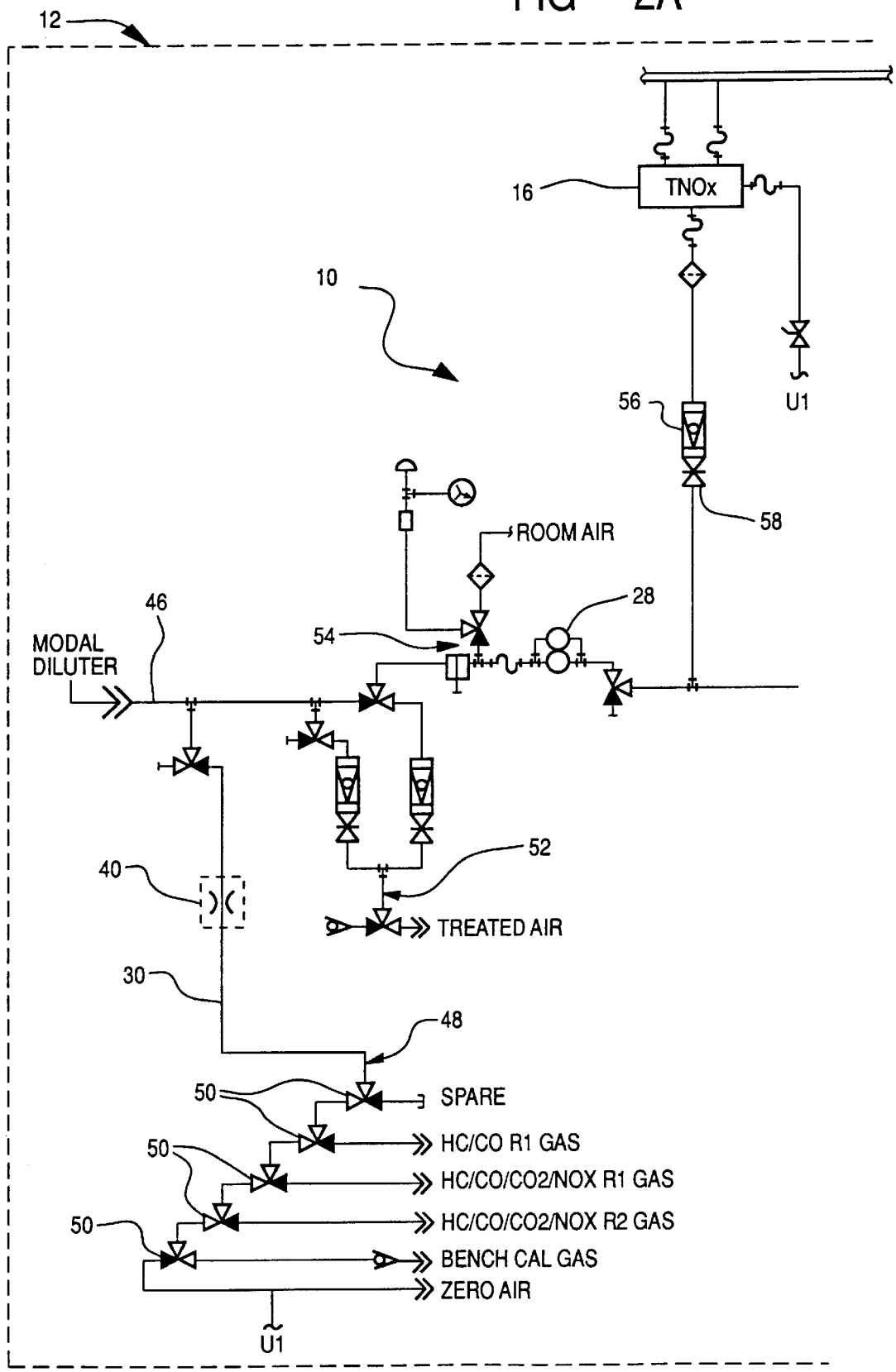
Figure 2B:
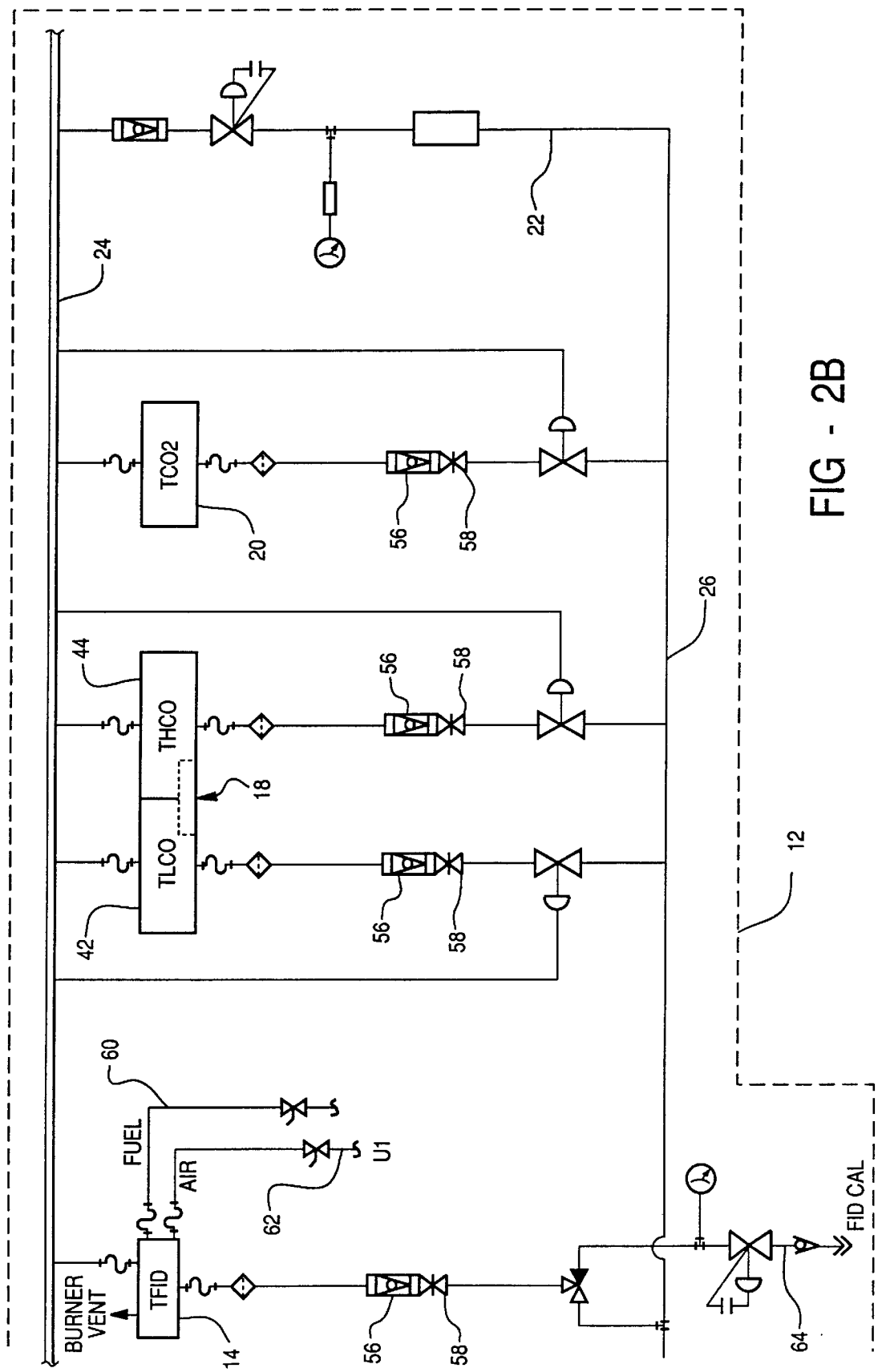

In FIGS. 2A–B, the bench 12 mounts a system 10 according to the invention as shown in the conceptual FIG. 1. The system includes equivalent TNOx, TFID, TCO and TCO2 analyzers 16, 14, 18, 20, respectively. The "T" prefix indicates that they are calibrated and intended for analyzing vehicle tailpipe emissions as opposed to bag (B), engine out (E) or intermediate (I—between converters in series) analyzers. The TCO analyzer 18 is dualed with separate low range (TLCO) 42 and high range (THCO) 44 units. A bypass line 22, exhaust header 24, supply header 26 and sample pump 28 are all included. A modal diluter 29 is not shown but is connected to a line 46 at the left of the drawing.

The blended span gas supply 30 is provided by a span tree 48 including a series of three way valves 50 connected to selectively supply several alternative blends of calibration span gas used for differing ranges of calibration as well as zero air (or optionally N2). A mass flow controller 40 meters the calibration gas to the system. Additional air supply means 52 and leak check means 54 are also connected upstream of the supply pump 28 which feeds the supply header 26. Each of the analyzer supply lines includes a flow meter 56 and a flow control valve 58 to control sample delivery. Separate connections for fuel supply 60, air supply 62 and special calibration gas 64 are also provided for-the FID analyzer.

Figure 3A:
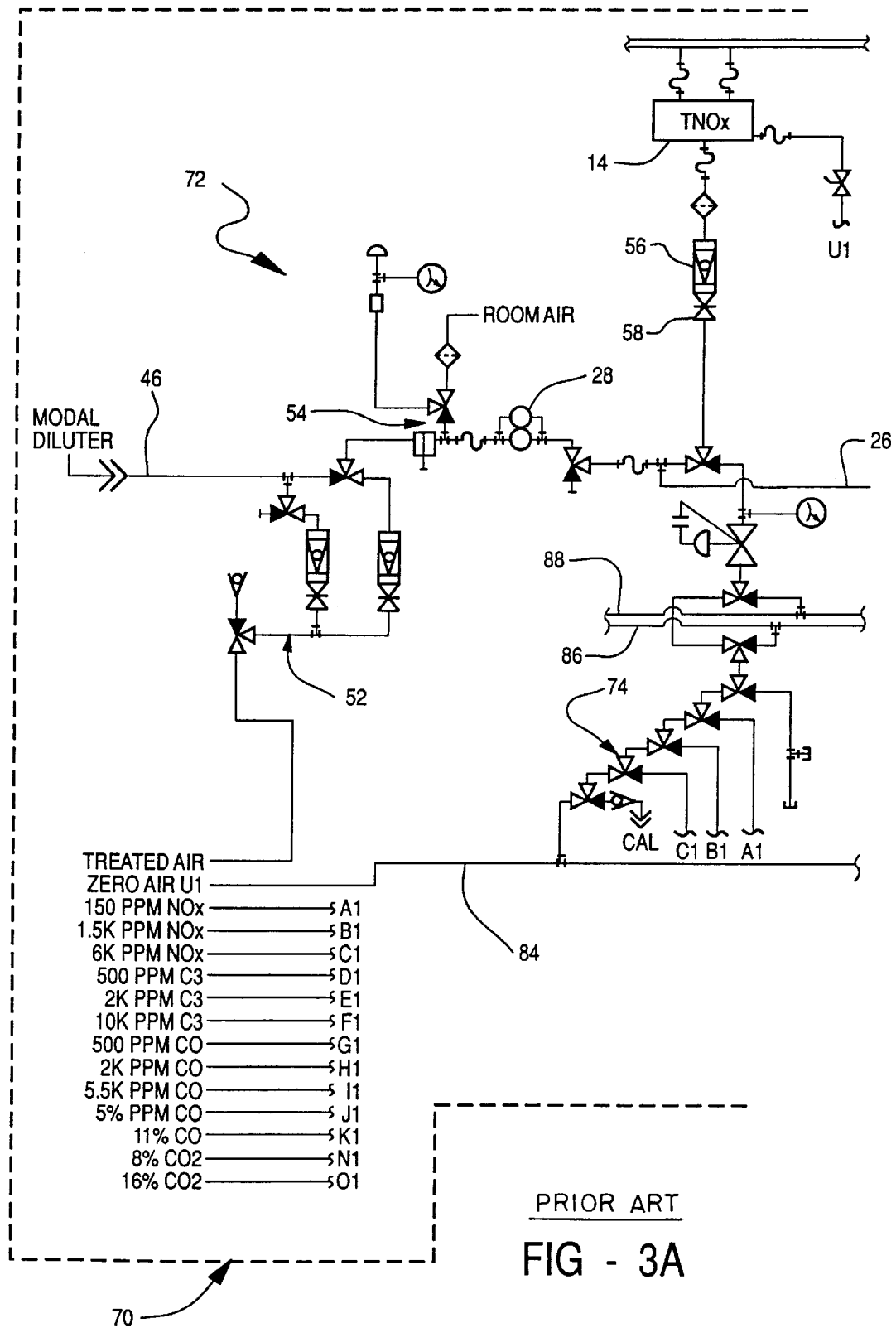
Figure 3B:
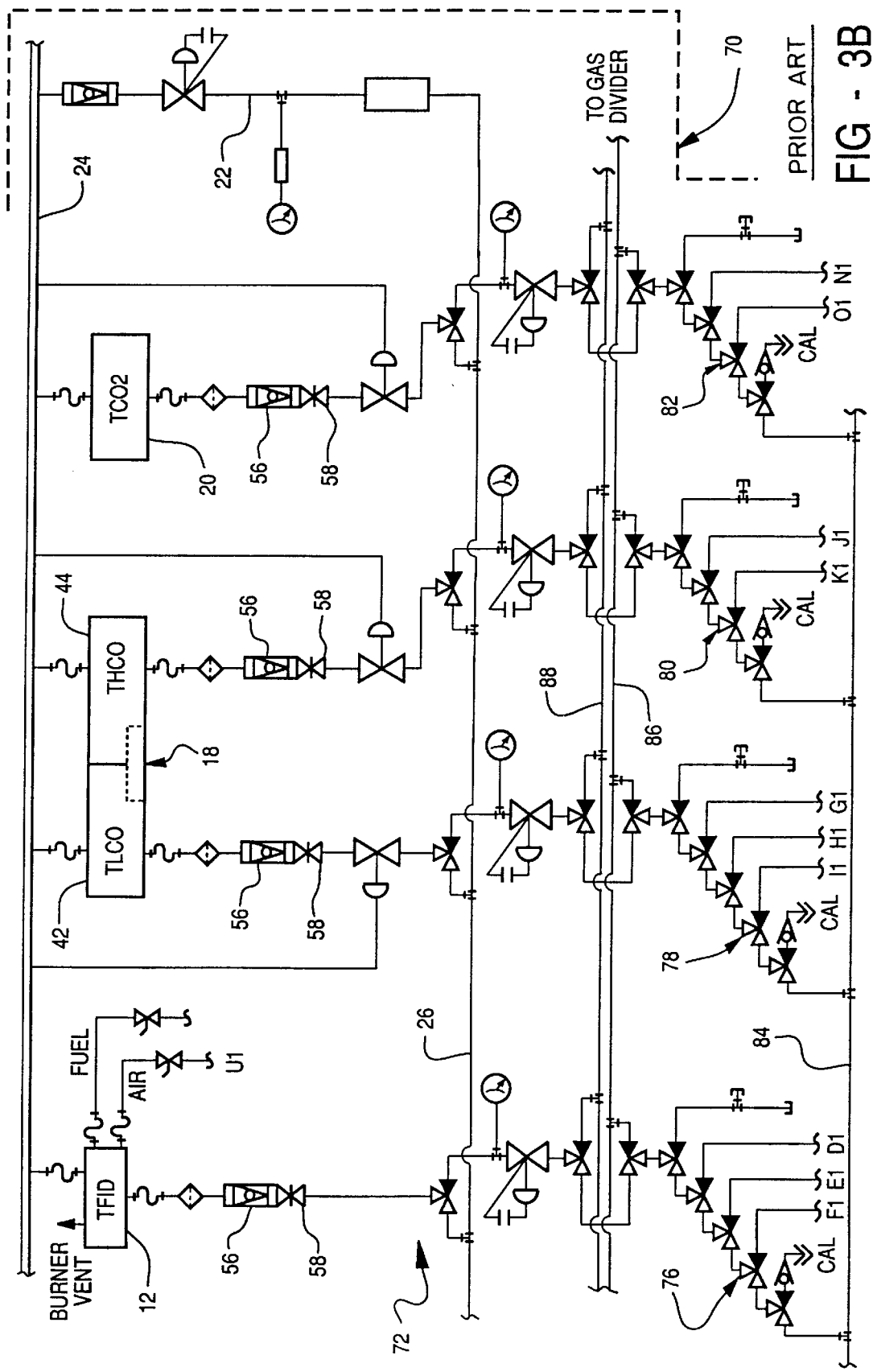

FIGS. 3A–B show a bench 70 mounting a prior art system 72 which includes many of the same components as in FIGS. 2A–B indicated by like reference numerals. However, instead of a single span tree 50 supplying calibration gas through a mass flow controller 40, the system 72 includes five separate span trees 74, 76, 78, 80, 82, connected respectively with the TNOx, TFID, TLCO, THCO and TCO2 analyzers 14, 12, 42, 44, 20, respectively. Each span tree provides a range of calibration span gases for calibrating its respective analyzer. Zero air is provided to the span trees through a manifold 84. The span trees also connect with their respective analyzers through a feed line 86 and a delivery line 88 with a highly accurate gas divider, not shown. The gas divider is used for dividing the full strength span gases (with predetermined dilution levels) to provide the intermediate percentage ratios of divided gas used for calibrating the intermediate points of the ranges of the respective analyzers.

Operation of the prior art system 72 of FIGS. 3A–B and the system 10 of the present invention shown in FIGS. 2A–B are as previously described. It is apparent that both the calibration procedures and the bench mounted system required are greatly simplified when constructed and operated according to the invention with an embodiment, for example, as shown in FIGS. 2A–B. The number of span trees is reduced from five, in the prior art embodiment of FIGS. 3A–B, to one in FIGS. 2A–B. Also, the gas divider is eliminated by using the FID analyzer to determine the actual percentage ratio of divided gas samples. Finally, the simultaneous calibration of all the analyzers made possible with the system of FIGS. 2A–B greatly reduces the time required for calibrating the system.

While the invention has been described by reference to certain preferred embodiments, it should be understood that numerous changes could be made within the spirit and scope of the inventive concepts described. Accordingly it is intended that the invention not be limited to the disclosed embodiments, but that it have the full scope permitted by the language of the following claims.

What is claimed is:

1. In a method for calibrating or diagnosing multiple engine exhaust gas analyzers responsive to HC, NOx, CO and CO2 constituent gases, the steps of:

providing a blended span gas comprising a known mixture of a zero gas with said constituent gases; and simultaneously supplying to all of said analyzers sequential samples of said blended span gas and selected divisions thereof for obtaining a series of simultaneous readings of the multiple analyzers for calibration or diagnostic purposes.

2. In a method for calibrating or diagnosing multiple engine exhaust gas analyzers responsive to NOx, CO and CO2 constituent gases, wherein an additional analyzer has an accurate known response, the steps of:

providing a blended span gas comprising a known mixture of a zero gas with said constituent gases;

simultaneously supplying to all of said analyzers sequential samples of said blended span gas and selected divisions thereof for obtaining a series of simultaneous readings of the multiple analyzers for calibration or diagnostic purposes;

preparing said divisions of the blended span gas to approximate proportions with a diluter; and utilizing the readings of said additional analyzer to accurately determine the proportions of the constituent gases in the various divisions of the blended span gas.

3. The steps of claim 2 wherein said accurate known response is obtained by precalibration of said additional analyzer.

4. The steps of claim 2 wherein said additional analyzer has a linear response.

5. The steps of claim 4 wherein said additional analyzer is a flame ionization detector for measuring hydrocarbon emissions.

6. In a method for calibrating or diagnosing multiple engine exhaust gas analyzers responsive to HC, NOx, CO and CO2 constituent gases, the steps of:

providing a blended span gas comprising a known mixture of a zero gas with said constituent gases; and simultaneously supplying to all of said analyzers at least one sample comprising a selected division of said blended span gas for obtaining simultaneous readings of the multiple analyzers for calibration or diagnostic purposes.

7. In a method for calibrating or diagnosing multiple engine exhaust gas analyzers responsive to HC, NOx, CO and CO2 constituent gases, wherein an additional analyzer has an accurate known response, the steps of:

providing a blended span gas comprising a known mixture of a zero gas with said constituent gases; and simultaneously supplying to all of said analyzers at least one sample comprising a selected division of said blended span gas for obtaining simultaneous readings of the multiple analyzers for calibration or diagnostic purposes preparing said division of the blended span gas to approximate proportions with a diluter; and utilizing the reading of said additional analyzer to accurately determine the proportions of the constituent gases in the division of the blended span gas.

8. The steps of claim 7 wherein said accurate known response is obtained by precalibration of said additional analyzer.

9. The steps of claim 7 wherein said additional analyzer has a linear response.

10. The steps of claim 9 wherein said additional analyzer is a flame ionization detector for measuring hydrocarbon emissions.

* * * * *